United States Patent
Castro (10) Patent No.: US 8,673,006 B2
(45) Date of Patent: Mar. 18, 2014

(54) SPINAL IMPLANT

(75) Inventor: Frank Castro, Louisville, KY (US)

(73) Assignee: IGIP, LLC, Louisville, KY (US)

( * ) Notice: Subject to any disclaimer, the term of this patent is extended or adjusted under 35 U.S.C. 154(b) by 598 days.

(21) Appl. No.: 12/804,867

(22) Filed: Jul. 30, 2010

(65) Prior Publication Data

US 2010/0305701 A1     Dec. 2, 2010

Related U.S. Application Data (63) Continuation-in-part of application No. 12/583,864, filed on Aug. 27, 2009, and a continuation-in-part of application No. 12/583,865, filed on Aug. 27, 2009, now Pat. No. 8,246,683, said application No. 12/583,864 is a continuation-in-part of application No. 12/290,069, filed on Oct. 27, 2008, now Pat. No. 8,226,718, said application No. 12/583,865 is a continuation-in-part of application No. 12/290,069, which is a continuation-in-part of application No. 12/221,779, filed on Aug. 6, 2008, now Pat. No. 8,002,832, which is a continuation of application No. 11/089,103, filed on Mar. 24, 2005, now Pat. No. 7,435,261.

(51) Int. Cl.
    *A61F 2/44*          (2006.01)

(52) U.S. Cl.
    USPC ..................... 623/17.11; 623/17.16

(58) Field of Classification Search
    USPC ............... 623/17.11–17.16; 606/75
    See application file for complete search history.

(56) References Cited

U.S. PATENT DOCUMENTS

| | | |
|---|---|---|
| 4,892,545 A | 1/1990 | Day et al. |
| 5,147,402 A | 9/1992 | Bohler et al. |
| 5,192,327 A | 3/1993 | Brantigan |
| 5,405,391 A | 4/1995 | Hednerson |
| 5,425,772 A | 6/1995 | Brantigan |
| 5,522,899 A | 6/1996 | Michelson |
| 5,558,674 A | 9/1996 | Heggeness et al. |
| 5,609,635 A | 3/1997 | Michelson |
| 5,766,252 A | 6/1998 | Henry et al. |
| 5,888,228 A * | 3/1999 | Knothe et al. ............. 623/17.16 |
| 5,980,522 A * | 11/1999 | Koros et al. ................ 623/17.11 |
| 6,066,175 A | 5/2000 | Henderson et al. |

(Continued)

FOREIGN PATENT DOCUMENTS

GB        2364643        2/2002

OTHER PUBLICATIONS

Barack, R. L. Revision Totatl Hip Arthroplasty: The Femoral Component. J. Am Acad Orthop Surg 1995; 3(2); 79-85. USA.

(Continued)

*Primary Examiner* — Jerry Cumberledge
(74) *Attorney, Agent, or Firm* — Kenneth F. Pearce (57) ABSTRACT

The present invention is a spinal implant that can be inserted into a surgically created cavity of one or more regions of the mammalian spine. Universal corner posts and one or more lateral universal posts are connected with a series of trapezoidal wedge-like braces. The series of braces includes a centralized brace, a first set of braces extending in a first direction away from the centralized brace and a second set of braces extending in a second direction away from the centralized brace. Embodiments of the current cage also include first and second lateral brakes and an end cap.

4 Claims, 10 Drawing Sheets

(56) References Cited

U.S. PATENT DOCUMENTS

| | | | |
|---|---|---|---|
| 6,080,193 | A | 6/2000 | Hochshuler et al. |
| 6,090,143 | A | 7/2000 | Meriwether et al. |
| 6,117,174 | A | 9/2000 | Nolan |
| 6,159,245 | A | 12/2000 | Meriwether et al. |
| 6,231,610 | B1 | 5/2001 | Geisler |
| 6,287,343 | B1 | 9/2001 | Kuslich et al. |
| 6,302,914 | B1 | 10/2001 | Michelson |
| 6,395,030 | B1 | 5/2002 | Songer et al. |
| 6,395,035 | B2 | 5/2002 | Bresina et al. |
| 6,409,766 | B1 | 6/2002 | Brett |
| 6,432,107 | B1 | 8/2002 | Ferree |
| 6,491,724 | B1 | 12/2002 | Ferree |
| 6,537,320 | B1 | 3/2003 | Michelson |
| 6,562,074 | B2 * | 5/2003 | Gerbec et al. ............. 623/17.15 |
| 6,569,201 | B2 | 5/2003 | Moumene et al. |
| 6,576,016 | B1 | 6/2003 | Hochshuler et al. |
| 6,613,091 | B1 * | 9/2003 | Zdeblick et al. ........... 623/17.16 |
| 6,641,614 | B1 | 11/2003 | Wagner et al. |
| 6,648,917 | B2 * | 11/2003 | Gerbec et al. ............. 623/17.11 |
| 6,660,038 | B2 | 12/2003 | Boyer et al. |
| 6,712,825 | B2 | 3/2004 | Aebi et al. |
| 6,712,852 | B1 | 3/2004 | Chung et al. |
| 6,746,484 | B1 | 6/2004 | Liu et al. |
| 6,761,738 | B1 | 7/2004 | Boyd |
| 6,767,367 | B1 | 7/2004 | Michelson |
| 6,776,798 | B2 | 8/2004 | Camino et al. |
| 6,805,714 | B2 | 10/2004 | Sutcliffe |
| 6,808,538 | B2 | 10/2004 | Papponneau |
| 6,837,905 | B1 | 1/2005 | Lieberman |
| 6,852,129 | B2 * | 2/2005 | Gerbec et al. ............. 623/17.15 |
| 6,863,673 | B2 | 3/2005 | Gerbec et al. |
| 6,926,737 | B2 | 8/2005 | Jackson et al. |
| 6,929,662 | B1 * | 8/2005 | Messerli et al. ........... 623/17.11 |
| 6,942,697 | B2 | 9/2005 | Lange et al. |
| 6,997,953 | B2 | 2/2006 | Chung et al. |
| D524,942 | S | 7/2006 | Felix |
| 7,166,110 | B2 | 1/2007 | Yundt |
| 7,182,782 | B2 | 2/2007 | Kirschman |
| 7,232,463 | B2 | 6/2007 | Falahee |
| 7,435,261 | B1 | 10/2008 | Castro |
| 7,618,460 | B2 | 11/2009 | Boyd |
| 7,621,953 | B2 * | 11/2009 | Braddock et al. ........... 623/17.11 |
| 7,641,701 | B2 | 1/2010 | Kirschman |
| 7,942,932 | B2 | 5/2011 | Castro |
| 8,002,832 | B2 | 8/2011 | Castro |
| 2002/0099443 | A1 * | 7/2002 | Messerli et al. ........... 623/17.11 |
| 2002/0128652 | A1 | 9/2002 | Ferree |
| 2003/0125739 | A1 | 7/2003 | Bagga et al. |
| 2003/0199980 | A1 * | 10/2003 | Siedler ....................... 623/17.11 |
| 2004/0064184 | A1 | 4/2004 | Chung et al. |
| 2004/0073314 | A1 | 4/2004 | White et al. |
| 2004/0126407 | A1 | 7/2004 | Falahee |
| 2004/0153155 | A1 | 8/2004 | Chung et al. |
| 2004/0153160 | A1 * | 8/2004 | Carrasco ..................... 623/17.15 |
| 2004/0199254 | A1 * | 10/2004 | Louis et al. ................. 623/17.11 |
| 2004/0199256 | A1 | 10/2004 | Wang |
| 2004/0204714 | A1 | 10/2004 | Liu et al. |
| 2004/0225360 | A1 | 11/2004 | Malone |
| 2005/0071006 | A1 | 3/2005 | Kirschman |
| 2005/0071008 | A1 | 3/2005 | Kirschman |
| 2005/0149192 | A1 | 7/2005 | Zucherman |
| 2005/0159813 | A1 | 7/2005 | Molz, IV et al. |
| 2006/0058879 | A1 * | 3/2006 | Metz-Stavenhagen .... 623/17.15 |
| 2006/0287725 | A1 | 12/2006 | Miller |
| 2007/0016295 | A1 | 1/2007 | Boyd |
| 2007/0123987 | A1 * | 5/2007 | Bernstein ................... 623/17.11 |
| 2007/0129805 | A1 | 6/2007 | Braddock, Jr. et al. |
| 2007/0250167 | A1 * | 10/2007 | Bray et al. ................. 623/17.11 |
| 2007/0255409 | A1 | 11/2007 | Dickson et al. |
| 2007/0255413 | A1 | 11/2007 | Edie et al. |
| 2008/0015694 | A1 | 1/2008 | Tribus |
| 2008/0021476 | A1 | 1/2008 | Kirschman |
| 2008/0132901 | A1 | 6/2008 | Recoules-Arche et al. |
| 2008/0154377 | A1 | 6/2008 | Voellmicke |
| 2008/0275506 | A1 | 11/2008 | Baynham et al. |
| 2009/0036985 | A1 | 2/2009 | Whiting |
| 2009/0234364 | A1 | 9/2009 | Crook |
| 2010/0004752 | A1 | 1/2010 | White et al. |

OTHER PUBLICATIONS

Castro, F. P., Jr. Stingers, Cervical Cord Neurapraxia, and Stenois. Clin Sport Med 2003; 22: 483-492. USA.

Majd M.E., Vadhva, M., Holt R.T. Anterior Cervical Reconstruction Using Titanium Cages With Anterior Plating. Spine 1999; 24 (15): 1604-1610. USA.

Park J.B., Cho Y.S., Riew, K.D. Development of Adjacent-Level Ossification in Patient with an Anterior Cervical Plate. J. Bone Surg. 1005; 87-A: 558-563. USA.

* cited by examiner

SPINAL IMPLANT

This Application is a Continuation-in-Part of Applications for Letters Patent Ser. No. 12/583,865 entitled—Spinal Implant—filed on Aug. 27, 2009 now U.S. Pat. No. 8,246,683 and Application for Letters Patent Ser. No. 12/583,864 entitled—Wedge-Like Spinal Implant—filed on Aug. 27, 2009, wherein the Applications for Letters Patent Ser. Nos. 12/583,864 and 12/583,865 are Continuations-in-Part of Application for Letters Patent, Ser. No. 12/290,069, entitled—Spinal Implant and Method of Using Spinal Implant—filed on Oct. 27, 2008 now U.S. Pat. No. 8,226,718 that is a Continuation-in-Part of Application for Letters Patent, Ser. No. 12/221,779, entitled—Spinal Implant and Method of Using Spinal Implant—filed on Aug. 6, 2008 now U.S. Pat. No. 8,002,832 that is a Continuation of Application for Letters Patent, Ser. No. 11/089,103, entitled—Spinal Implant and Method of Using Spinal Implant—filed on Mar. 24, 2005, now U.S. Pat. No. 7,435,261 B2 issued on Oct. 14, 2008.

BACKGROUND OF THE INVENTION

A. Field of the Invention

Among other things, the present invention is related to a surgical implant or cage that can be inserted into a cavity that has been created by removing spinal tissue. The generally wedge-like trapezoidal shaped cage includes a series of trapezoidal dividers or braces, first and second universal corner posts and lateral universal posts manufactured in such a way that the surgeon can see through the cage's openings prior to the addition of substances. First and second lateral brakes are incorporated into the spinal implant, and the lateral brakes can include one or more bores for receiving fasteners. Select preferred embodiments of the current spinal implant can be provided with superior and inferior plates having bores that can receive fasteners. Still other preferred embodiments utilize one or more brakes that are connectable to the lateral supports of the spinal implant. And still other preferred embodiments can employ an end cap to assists with the stabilization of the spinal implant in a surgically created cavity.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

1) U.S. Published Patent Application No. 20030125739 A1—Bagga, et al. discloses a bioactive spinal implant and method of manufacture. Among other things, it does not appear that the Bagga invention practices the use of a series of dividers, universal corner posts, universal posts or bars.

2) U.S. Pat. No. 6,767,367 B1—Michelson enables a spinal fusion implant having deployable bone engaging projections. Michelson teaches that the '367 implant 300 has a rotatable member 320 that is preferably frustoconical in shape. Rotatable member 320 has bone engaging projections 332 adapted to penetrably engage the bone of the adjacent vertebral bodies. Bone engaging projections 332 are preferably configured such that in a retracted position, implant 300 may be linearly inserted into the disc space. After implant 300 is inserted into the disc space, bone engaging projections 332 are moved to a deployed position to penetrably engage the endplates of each adjacent vertebral body and prevent the expulsion of implant 300 from the disc space.

3) U.S. Pat. No. 6,537,320 B1—Michelson enables a self-broaching, rotatable, push-in interbody spinal fusion implant and method for its deployment. Among other things, it does not appear that the Michelson invention practices the use of a series of dividers, universal corner posts, universal posts or bars.

4) U.S. Pat. No. 5,609,635—Michelson enables a lordotic interbody spinal fusion implant. The Michelson Summary of the Invention teaches, "In the preferred embodiment of the modular implant, the implant is again wedge-shaped in the side elevational view and is taller at its insertion end than at its trailing end." Being taller at an insertion end than at the trailing end is a teaching that is incompatible with the current spinal implant. Further, among other things, it does not appear that the Michelson invention practices the use of a series of dividers, universal corner posts, universal posts or bars.

5) U.S. Pat. No. 6,302,914 B1—Michelson enables a lordotic interbody spinal fusion implant. The '914 patent is a continuation patent of the U.S. Pat. No. 5,609,635—Michelson patent and enables the same limitations as the '635 patent.

6) U.S. Pat. No. 6,066,175—Henderson, et al. enables a fusion stabilization chamber. Henderson discloses a mesh cage 41, barrel vaults 48 and 49 and flanges 50 and 51 to anchor the cage. The cage is preferably rectangular when viewed from the top or the bottom. Among other things, it does not appear that the Henderson invention practices the use of a series of dividers, universal corner posts, universal posts or bars.

7) U.S. Pat. No. 5,766,252—Henry, et al. enables an interbody spinal prosthetic implant and method. Henry requires a threaded hole 38 to practice the '252 invention. Among other things, it does not appear that the Henry invention practices the use of a series of dividers, universal corner posts, universal posts or bars.

8) U.S. Pat. No. 5,425,772—Brantigan enables a prosthetic implant for intervertebral spinal fusion. The '772 device practices traverse teeth or serrations 19 where the teeth have sharp peaks 19a, slopping walls 19b and valleys 19c. Among other things, it does not appear that the Brantigan invention practices the use of a series of dividers, universal corner posts, universal posts or bars.

9) U.S. Pat. No. 5,147,402—Bohler, et al. enables an implant for ingrowth of osseous tissue. Among other things, it does not appear that the Bohler invention practices the use of a series of dividers, universal corner posts, universal posts or bars.

10) U.S. Pat. No. 6,746,484—Liu, et al. enables a spinal implant. Among other things, Liu teaches an implant 1 having an elongate hollow body 3, parallel longitudinal walls 4 and terminal ends 5 and 6 including threaded holes 11a. Among other things, it does not appear that the Liu invention practices the use of a series of dividers, universal corner posts, universal posts or bars.

11) U.S. Pat. No. 6,231,610 B1—Geisler enables an anterior cervical column support device. The '610 apparatus utilizes serrations on the load bearing surfaces and two screw holes. Among other things, it does not appear that the Geisler invention practices the use of a series of dividers, universal corner posts, universal posts or bars.

12) U.S. Pat. No. 6,660,038 B2—Boyer, et al. enables skeletal reconstruction cages. The Boyer patent discloses an end cap 210 suitable for coupling to central shaft 160 includes an outer wall 212, as well as a central hole disposed along axis 213 with a lower inner wall 214, an upper inner wall 216, and an inner ridge portion 218. Notably, while outer wall 176 of central shaft 160 is generally circular, outer wall 212 of end cap 210 is generally oblong, so that a generally I-shaped skeletal reconstruction cage may be formed when a pair of end caps 210 are placed on central shaft 160. Among other things, it does not appear that the Boyer invention practices the use of a series of dividers, universal corner posts, universal posts or bars.

13) U.S. Pat. No. 6,491,724—Ferree enables a spinal fusion cage with lordosis correction. Among other things, Ferree teaches an anterior portion 112 that includes mating members 120 and 122 with teeth 124 or other features to form a locking or ratchet mechanism that is used to alter the height of the cage. Among other things, it does not appear that the Ferree invention practices the use of a series of dividers, universal corner posts, universal posts or bars.

14) U.S. Pat. No. 6,117,174—Nolan enables a spinal implant device that has disc 14 made of the same material as body 12. Among other things, it does not appear that the Nolan invention practices the use of a series of dividers, universal corner posts, universal posts or bars.

15) U.S. Published Patent Application No. 20070016295—Boyd discloses a reinforced molded implant formed of cortical bone. Boyd reads, "Implant 10 defines a longitudinal axis 11 and includes a first strut 12, a second strut 14 spaced from first strut 12, and cross-member 16 extending therebetween. First strut 12 and second strut 14 are each positioned to lie in a plane substantially parallel to longitudinal axis 11. Implant 10 includes at least one additional cross-member 16A connecting first strut 12 and second strut 14. It is understood that in alternative embodiments implant 10 can have one or a plurality of cross-members connecting first strut 12 to second strut 14."

16) U.S. Pat. No. 6,090,143—Meriwether, et al. enables a box cage for intervertebral body fusion. Meriwether reads, "FIG. 6 illustrates a further embodiment of the invention which is a slight modification of that shown in FIG. 4. In the embodiment of FIG. 6, rather than having a rectangular longitudinal cross-section, it is trapezoidal such that the resulting cage member, indicated generally by numeral 110, is wedge-shaped. The assembled cage comprises a box-like base 112 and a cover 114 dimensioned to fit over the base much like the cover on a shirt box. The height dimension of the rightmost ends of the base and cover are greater than the height dimension of the corresponding, opposed left side ends, thus providing the desired wedge shape. Upwardly projecting ribs 116 and 118 extend along the rear and front side edges, respectfully, and likewise, the base 112 includes longitudinally extending ribs 120 and 122 projecting downwardly from the undersurface of the base along the side edges thereof The right and left ends of the base 112 and the cover 114 include semi-circular cut-outs as at 124 and 126 and 128-130 such that when the cover 114 is placed upon the base 112, circular apertures are formed. These apertures are adapted to receive a tapered screw 132 therein. The slope of the taper of the screw is designed to correspond to that of the cage assembly 110 such that when the screw 132 is threaded into the circular opening defined by arcuate cut-outs 124 and 126 and advanced by turning until the leading end 134 of the screw enters the circular aperture 128-130, further turning of the screw will raise the case cover 114 relative to its base 112, allowing adjustment of the cage height following positioning thereof between adjacent vertebral bodies."

17) U.S. Pat. No. 6,159,245—Meriwether, et al. enables a box cage for intervertebral body fusion. The '245 Meriwether patent is a continuation of U.S. Pat. No. 6,090,143—Meriwether, et al. and teaches the same limitations as the '143 patent.

18) U.S. Pat. No. 6,432,107—Ferree enables enhanced surface area spinal fusion devices. The '107 patent teaches, "The device 200 fits into slots 204 and 206 made in upper and lower vertebrae 208 and 210, respectively, allowing the lower section to fuse within the body of the lower vertebrae 210, and the upper section to fuse within the body of the upper vertebrae 208. Thus, in contrast to existing devices, the device 200 and the alternative embodiments disclosed herein feature considerably more intimate contact with cancellous bone due to the fact that the device is inserted directly into the cavities 204 and 206. Rather than a relatively minor amount of scraping of the end plates of the vertebrae to be distracted, the entire end portions of the device 200 which penetrate the upper and lower vertebrae make contact with cancellous bone, thereby enhancing fusion considerably. FIG. 2B is a cross-section of a vertebrae of FIG. 2A as viewed from a top-down perspective, showing how the device fits tightly along the entire walls of the channels created in the vertebrae." Among other things, the Ferree device does provide a series of dividers or receptacles visible to the surgeon after insertion into the surgical cavity.

19) U.S. Pat. No. 6,569,201—Moumene, et al. enables a hybrid composite interbody fusion device. Moumene's Osteoconductive pore 2 forms a void 23 within the support and defines an inner surface 13, and opens onto side surface openings 19, 21 formed in side surfaces 7, 9, and the void section 23 is suitable for housing a bone growth material such as bone chips (not shown). Among other things, it does not appear that the Moumene invention practices the use of a series of dividers, universal corner posts, universal posts or bars.

SUMMARY OF THE INVENTION

Unlike traditional spinal implants, the present invention provides a spinal implant that can be packed with bone graft and/or other osteogenic materials or other substances after the spinal implant has been inserted into a cavity created by the removal of spinal tissue. After the implant is inserted into the surgically created cavity and prior to insertion of osteogenic substances, the surgeon can view the dura mater of the spinal cord. During surgical procedures, the trapezoidal-like cage assists the surgical team in not impinging the spinal cord with the implant. Post operative and prior to complete arthrodesis, the generally wedge-like implant inhibits extrusion of the cage against the spinal cord. Select preferred embodiments employ an end cap to assist with the stabilization of the spinal implant.

An aspect of the present invention is to provide a generally wedge-like cage.

Still another aspect of the present invention is to provide a spinal implant having a series of trapezoidal dividers or braces, first and second universal corner posts and lateral universal posts.

It is still another aspect of the present invention to provide an implant having select embodiments that can be implanted through the patient's frontal or rearward side.

Yet still another aspect of the present invention is to provide a cage that can be severed across a first cross-section or severed across a first cross-section and a second cross-section to create a custom fitted implant for the surgically created cavity.

Still another aspect of the present invention is to provide a cage including a generally straight brace, a first set of braces diverging away from the horizontal and a second set of braces diverging away from the horizontal.

It is still another aspect of the present invention to provide an implant having a plurality of apertures the surgeon can see through prior to addition of osteogenic and/or arthrodesis accelerating substances or other substances.

Yet still another aspect of the present invention is to provide a cage having a first lateral brake and a second lateral brake.

It is another aspect of the present invention to provide an implant where the first and second lateral brakes include one or more bores for receiving fasteners such as bone screws.

Yet another aspect of the present invention is to provide an implant that includes upper and lower plates having one or more bores for receiving fasteners.

It is still another aspect of the present invention to provide a brake that is manufactured separately from the spinal implant, where the brake is connectable to the spinal implant.

Still another aspect of the present invention is to provide a connectable brake that includes one or more bores for receiving fasteners.

Yet another aspect of the present invention is to provide an end cap attachable to vertebra for assisting with the stabilization of the spinal implant.

It is still another aspect of the present invention to provide an end cap capable of increasing the length of the spinal implant.

Still another aspect of the present invention is to provide a spinal implant capable of enhancing lordosis.

An embodiment of the current invention can be described as a spinal implant consisting essentially of titanium, stainless steel, resorbable polymers, non-resorbable polymers or combinations thereof; the spinal implant comprising a length of consecutively joined receptacles having peripheral openings a surgeon can see through prior to addition of osteogenic and/or arthrodesis accelerating substances, wherein the length of consecutively joined receptacles comprises: a) a series of trapezoidal dividers having a common lengthwise axis, wherein each divider comprises: i) an inward side; ii) an outward side; iii) a first side connected with the outward side and the inward side forming a first outward corner with the outward side and a first inward corner with the inward side; iv) a second side connected with the outward side and the inward side forming a second outward corner with said outward side and a second inward corner with the inward side; and v) an aperture; b) a first universal corner post contacting the first inward corners; c) a second universal corner post contacting the second inward corners; d) one or more first universal posts contacting the first sides of said dividers; e) one or more second universal posts contacting the second sides of said dividers; f) one or more inward universal posts contacting the inward sides of the dividers; g) a first brake extending laterally beyond the first sides and from about a superior member of the series to about an inferior member of the series, wherein the first brake comprises one or more bores; and h) a second brake extending laterally beyond the second sides and from about the superior member of the series to about the inferior member of the series, wherein the second brake comprises one or more bores.

Another embodiment of the current invention can be described as a cage including peripheral openings a surgeon can see through prior to addition of osteogenic and/or arthrodesis accelerating substances and capable of implantation into a cavity surgically created between a superior spinal region and an inferior spinal region of a mammal; the cage comprising: a) a series of trapezoidal dividers, wherein each the divider comprises an inward side, an outward side and opposing first and second lateral sides such that a combination of the sides creates an aperture; b) a first universal corner post contacting first inward corners of the series; c) a second universal corner post contacting second inward corners of the series; d) one or more first universal posts contacting first lateral sides of the series; e) one or more second universal posts contacting second lateral sides of the series; f) one or more inward universal posts contacting inward sides of the series; g) a first brake comprising one or more bores and extending laterally beyond the first lateral sides of the series and from about a superior member of the series to about an inferior member of the series; and h) a second brake comprising one or more bores extending laterally beyond the second lateral sides of the series and from about the superior member of the series to about the inferior member of the series.

Still another embodiment of the current invention can be described as a cage capable of implantation into a cavity surgically created between a superior spinal region and an inferior spinal region of a mammal; the cage comprising: a) a series of trapezoidal braces, wherein each trapezoidal brace includes two sides of equal length and an aperture; b) an inward support; c) an outward support; d) a first lateral support; e) a second lateral support, wherein the supports are joined with each other such that the outward support is of greater dimensions than the inward support; f) a first brake comprising one or more bores and extending laterally beyond the first lateral support of the series and from about a superior member of the series to about an inferior member of the series; and g) a second brake comprising one or more bores and extending laterally beyond the second lateral support of the series and from about the superior member of the series to about the inferior member of the series.

Yet another embodiment of the current invention can be described as a brake attachable to a spinal implant, wherein the spinal implant comprises a lateral support including a plurality of lengthwise posts and one or more spaces associated with said plurality of lengthwise posts; the brake comprising: a) an inward side and an outward side; b) a length approximating the length of the lateral support; c) a width extending laterally and outwardly from the lateral support, after attachment to the lateral support; d) one or more bores for receiving fasteners; and e) one or more clips attached to the inward side for cooperating with one of the posts and spaces adjacent the post.

Still another embodiment of the current invention can be described as a brake attachable to a spinal cage, comprising: a) an inward side and an outward side; b) a width extending laterally and outwardly from the spinal cage; c) one or more bores for receiving fasteners; and d) one or more connectors attached to the inward side for connecting the brake to one or more universal posts.

Yet still another embodiment of the current invention can be described as an end cap for a spinal implant comprising: a) a coupler comprising: i) a spacer; ii) a frontal plate including at least one opening for receiving a fastener for securing the coupler to vertebra; and iii) pins attached perpendicularly to and extending away from an inward side of the spacer; and b) a bridge comprising: i) an outermost section surrounding a generally trapezoidal aperture; the outermost section further comprising; A) a surgeon facing side including a plurality of bores for receiving the pins; and B) a spinal implant facing side including bores therein; and ii) docking slides for securely engaging a corresponding opening proximate a lengthwise end of the spinal implant.

Yet another embodiment of the current invention can be described as an end cap for a spinal implant comprising: a) a coupler comprising: i) a frontal plate including at least one opening for receiving a fastener for securing the coupler to vertebra; and ii) one or more extensions; and b) a bridge comprising: i) bores for receiving the extensions; and ii) slides for securely engaging a corresponding opening proximate a lengthwise end of the spinal implant.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention.

In the most general sense, the present invention is a cage or implant that can be inserted into a cavity of the spinal column. Surgical removal of mammalian spinal tissue in one or more spinal regions creates the cavity or cavities that will receive the implant or implants. It has been discovered that many embodiments of the current implant can be useful for cervical spine surgeries and can assist in stabilization of the postoperative spine. And many of the preferred embodiments of the present invention are particularly suited for corpectomy or partial corpectomy procedures.

After insertion of the implant into the cavity, the cage assists in stabilizing the spinal column against rotational movement and also resists the compression forces associated with gravity on the spinal column. Select preferred embodiments of the present invention can be implanted through the patient's anterior side, e.g., the frontal side of the patient's neck. The current spinal implants are custom fitted for the surgical cavity into which they will be inserted, i.e., the cage can be manufactured to fit the surgical cavity or the cage can be severed across a first cross section or the cage can be severed across first and second cross sections to size the cage to fit the cavity.

Preferred embodiments of the current spinal implant are generally trapezoidal in shape and are manufactured of titanium alloys, stainless steel, resorbable polymers, non-resorbable polymers or any other composition acceptable in the art. Within the scope of the present invention, it has advantageously been discovered that the cage can have a width of from about six to about fifteen millimeters, as measured along the narrowest parallel of the trapezoid, and a depth of from about eight millimeters to about fifteen millimeters, as measured along a converging side of the trapezoid. Generally the spacing between dividers of the cage is approximately twelve millimeters, as measured from outward side to outward side of the series of dividers. Openings of the sides of the cages of the current invention into which bone graft, osteogenic and/or arthrodesis accelerating substances are packed can have areas from about 36 millimeters$^2$ to 225 millimeters$^2$ or greater.

Universal corner posts and lateral universal posts are spaced about the outer border of the cage. Select preferred embodiments include one or more ties extending about the implant and contacting the universal posts and the universal corner posts. Universal corner posts and universal posts are from about one millimeter to about two millimeters wide and are situated along the outer periphery of the cage in such a way as to create apertures between the universal lateral posts and the universal corner posts. Depending on the volume of the implant, spacing between the universal corner posts and the lateral universal posts and between the lateral universal posts is from about one millimeter to about two millimeters.

Meeting a long felt but unfilled need in the spinal surgical arts, the unique structures of the present invention allow the surgical team to view the dura mater, before the cage is packed with bone graft, osteogenic and/or arthrodesis accelerating substances. Allowing the surgical team to view the dura mater while inserting the implant into the cavity reduces the possibility of having the cage inadvertently contact or injure the spinal cord. Contact between the surgical cavity wall and the wedge-like cage can also inhibit the implant from contacting the spinal cord. It appears that having the apertures of select embodiments in such close proximity with the cavity's walls increases the probability of the osteogenic materials procuring a blood supply. And it is believed that increasing the blood supply to the osteogenic materials held by the cage enhances local areas of arthrodesis between the vertebra and the bone graft. Preferred embodiments of the present invention are provided with lateral brakes to further impede the implant from contacting the spinal column.

Figures 1, 2:
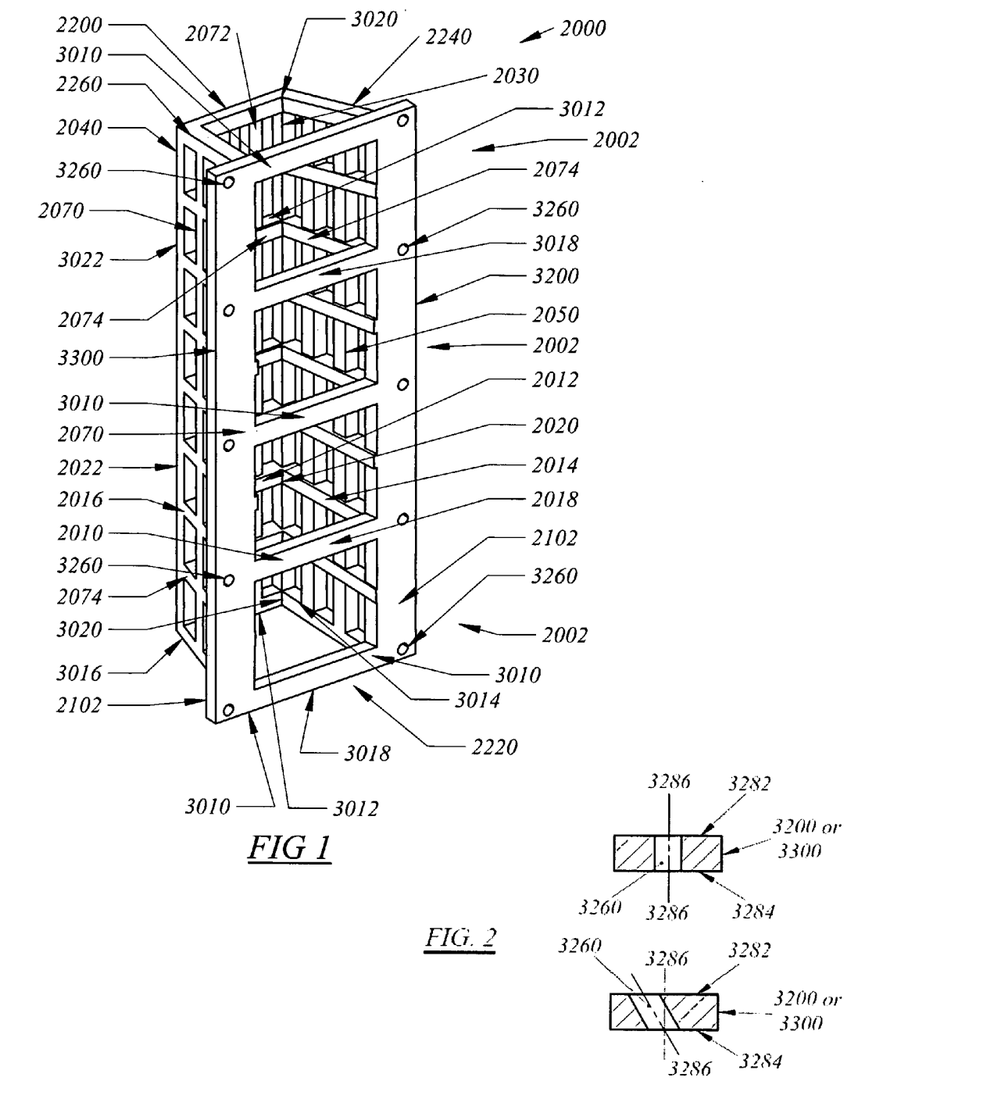
FIG. 1 is a frontal perspective of an embodiment of the present invention.
FIG. 2 is a cross section of an embodiment of a brake of the present invention.

Among other things, FIG. 1 enables a cage (2000) having a series of trapezoidal dividers or braces (2010) and (3010) and a plurality of receptacles (2002) that can be packed with osteogenic materials, arthrodesis accelerating substances or other substances prior to the completion of spinal surgery. Cage (2000) is manufactured of titanium, stainless steel, resorbable polymers, non-resorbable polymers or combinations thereof. By way of illustration, generally horizontal divider or brace (2010) has inward side (2012) (after insertion into the surgically created cavity, positioned near the dura mater of the spinal cord), outward side (2018) (proximate the surgeon after insertion into the surgically created cavity), first converging or lateral side (2014) and second converging or lateral side' (2016). Intersection of first lateral side (2014) and inward side (2012) creates first corner (2020) and intersection of inward side (2012) and second lateral side (2016) creates second corner (2022), such that straight brace (2010) has first corner (2020) and second corner (2022).

A first set of braces or dividers (3010) is positioned in a first direction away from straight brace or generally horizontal divider (2010) and a second set of braces or dividers (3010) is positioned in a second direction away from straight brace or generally horizontal divider (2010). Although not shown in FIG. 1, other preferred embodiments of cage (2000) can have a single brace (3010) extending in a first direction away from straight brace (2010) and a single brace (3010) extending in a second direction away from straight brace (2010). Each brace (3010) has inward side (3012), first lateral side (3014), second lateral side (3016) and outward side (3018). Intersection of first converging sides (3014) and inward sides (3012) create first corners (3020) and intersection of inward sides (3012) and second converging sides (3016) create second corners (3022), such that each brace (3010) has first corner (3020) and second corner (3022). First universal corner post (2030) contacts first corners (2020 and 3020) and second universal corner post (2040) contacts second corners (2022 and 3022). In the embodiment disclosed in FIG. 1, first universal corner post (2030) is angled at about ninety degrees to simultaneously connect with inward side (2012) and first lateral side (2014) of generally horizontal divider (2010) and inward sides (3012) and first lateral sides (3014) of dividers (3010). Second universal corner post (2040) is angled at about ninety degrees to simultaneously connect with inward side (2012) and second lateral side (2016) of straight brace (2010) and inward sides (3012) and second lateral sides (3016) of braces (3010).

In select embodiments, one or more first side universal posts (2050) contact first lateral sides (2014 and 3014) of cage (2000), one or more second side universal posts (2070) contact second lateral sides (2016 and 3016) of cage (2000) and one or more inward universal posts (2072) contact inward sides (2012 and 3012) of cage (2000). One of the first side universal posts (2050) is generally proximate outward side (2018) of brace (2010) and outward sides (3018) of braces (3010). In a similar vein, one of the second side universal posts (2070) is generally proximate outward side (2018) of brace (2010) and outward sides (3018) of braces (3010).

Inward support (2200) of cage (2000) includes inward side (2012) of straight brace (2010), inward sides (3012) of braces (3010) and universal corner posts (2030 and 2040). First lateral support (2240) of cage (2000) includes lateral side (2014) of straight brace (2010), lateral sides (3014) of braces (3010), universal corner post (2030) and one or more universal posts (2050). Second lateral support (2260) of cage (2000) includes lateral side (2016) of straight brace (2010), lateral sides (3016) of braces (3010), universal corner post (2040) and one or more universal posts (2070). Outward support (2220) of cage (2000) includes outward side (2018) of straight brace (2010), outward sides (3018) of braces (3010), an outward universal post (2050) and an outward universal post (2070).

Select preferred embodiments of cage (2000) can also include inward universal posts (2072) contacting generally inward side (2012) of generally horizontal divider (2010) and inward sides (3012) of dividers (3010). Still other preferred embodiments of cage (2000) can include one or more ties (2074) contacting universal corner posts (2030, 2040) and universal posts (2050, 2070 and 2072). Most preferably, ties (2074) are positioned on the inward sides of the universal posts (2030, 2040, 2050, 2070 and 2072).

The combination of straight brace (2010), braces (3010), universal corner posts (2030 and 2040), universal posts (2050, 2070 and 2072) and ties (2074) creates openings of more than one cross-sectional area about the outer border of cage (2000)—allowing the surgeon to see through the openings, prior to the addition of osteogenic or other substances into implant (2000).

In the preferred embodiment exemplified in FIG. 1, cage (2000) is provided with first lateral brake (3200) and second lateral brake (3300). Lateral brakes (3200 and 3300) assist the surgeon in minimizing potential damage to the spinal cord from over-insertion of implant (2000) into a surgically created cavity. First lateral brake (3200) extends laterally beyond first lateral sides (2014 and 3014) of braces (2010 and 3010) and second lateral brake (3300) extends laterally beyond second lateral sides (2016 and 3016) of braces (2010 and 3010) of implant (2000). In select preferred embodiments, lateral brakes (3200 and 3300) can also form part of outward support (2220) of cage (2000). Through experimentation and testing, it has been discovered that an optimal functionality of the present invention can be achieved when lateral brakes (3200 and 3300) are extended laterally from about one millimeter to about six millimeters beyond the lateral sides of cage (2000).

In select preferred embodiments, lateral brake (3200) is integral with outward universal post (2050) and lateral brake (3300) is integral with outward universal post (2070). As shown in FIG. 1, first lateral brake (3200) runs generally vertically from about superior brace or superior member (3010) of the series of trapezoidal braces (2010 and 3010) to about inferior brace or inferior member (3010) of the series of trapezoidal braces (2010 and 3010). Second lateral brake (3300) runs from about superior member (3010) of the series of trapezoidal braces (2010 and 3010) to about inferior member (3010) of the series of trapezoidal braces (2010 and 3010).

As shown in FIG. 1, lateral brakes (3200 and 3300) are provided with one or more bores (3260). Depending on predetermined engineering parameters and as shown in FIG. 2, first lateral brake (3200) and/or second lateral brake (3300) can include one or more bores (3260) that are perpendicular to outward sides (3282) and inward sides (3284) of lateral brakes (3200 and 3300). In select preferred embodiments, lateral brakes (3200 and 3300) can include one or more bores (3260) that are angled at other than perpendicular from the outward sides (3282) and inward sides (3284) of lateral brakes (3200 and 3300). It has been discovered that bores (3260) can be angled from about 1 degree to about 60 degrees away from the bore's reference axis (3286-3286), where the reference axis (3286-3286) equates to the perpendicular axis between outward sides (3282) and inward sides (3284) of lateral brakes (3200 and 3300). In select preferred embodiments, bores (3260) of lateral brakes (3200 and 3300) proximate superior member (3010) of the series of trapezoidal braces (2010 and 3010) are angled upward and bores (3260) proximate inferior member (3010) of the series of trapezoidal braces (2010 and 3010) are angled downward. Bores (3260) function to receive a fastener, such as a screw (not shown in this view), that assists in securing the implant to bone.

Figure 3:
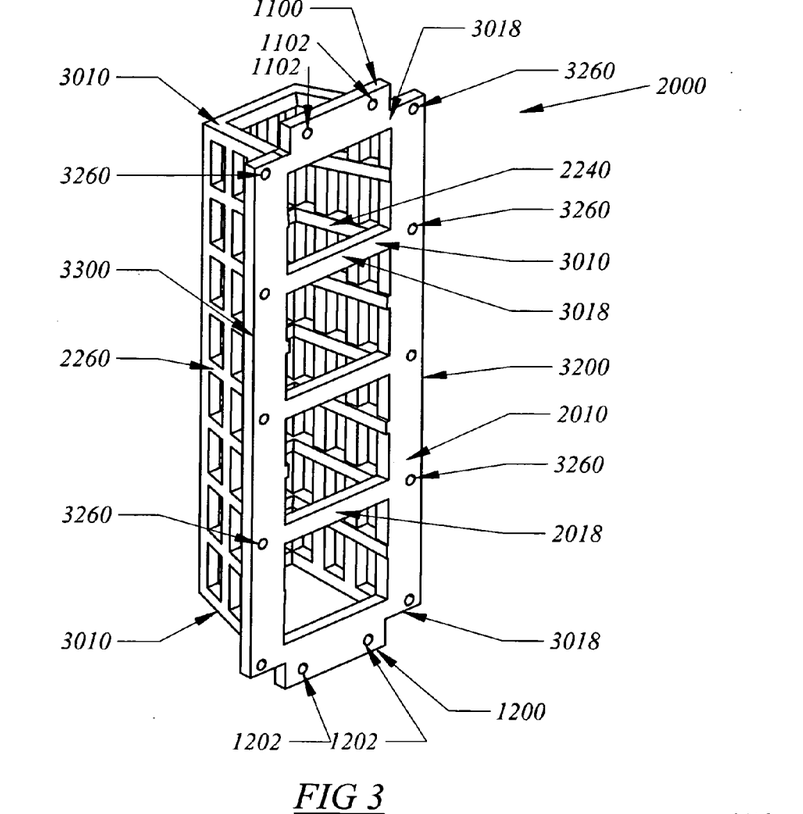
FIG. 3 is a frontal perspective of another embodiment of the present invention.

The preferred embodiment disclosed in FIG. 3 that is similar to the preferred embodiment disclosed in FIG. 1. The FIG. 3 embodiment portrays cage (2000) having first lateral brake (3200) and second lateral brake (3300). First lateral brake (3200) extends laterally beyond first lateral support (2240) of cage (2000) and second lateral brake (3300) extends laterally beyond lateral support (2260) of cage (2000). First lateral brake (3200) and second lateral brake (3300) are provided with one or more bores (3260).

As shown in FIG. 3, implant (2000) is also provided with a superior plate (1100) extending upward from superior member (3010) of the series of trapezoidal braces (2010 and 3010).

In similar fashion, inferior plate (1200) depends downwardly from inferior member (3010) of the series of trapezoidal braces (2010 and 3010). Upper plate (1100) has two bores (1102) for receiving fasteners, such as screws, to assist in securing cage (2000) to bone. Lower plate (1200) includes two bores (1202) for receiving fasteners that assist in securing cage (2000) to bone. Although upper plate (1100) and lower plate (1200) are shown with a plurality of bores, Applicant's current invention can function when upper plate (1100) and lower plate (1200) each include only a single bore (1102, 1202) or no bores.

In select embodiments, superior plate (1100) extends upward in a plane perpendicular to outward side (3018) of superior member (3010) and inferior plate (1200) depends downward in a plane perpendicular to outward side (3018) of inferior member (3010). Although not shown FIG. 3, in other embodiments, plate (1100) can be extended 2-3 millimeters outward from superior member (3010) before plate (1100) extends upward from superior member (3010). In a similar manner, inferior plate (1200) can be extended 2-3 millimeters outward from inferior member (3010) before plate (1200) depends downward from inferior member (3010). When the need arises, outward extension of superior plate (1100) and inferior plate (1200) allows cage (2000) to securely fit within a deeper surgical cavity.

Figure 4:
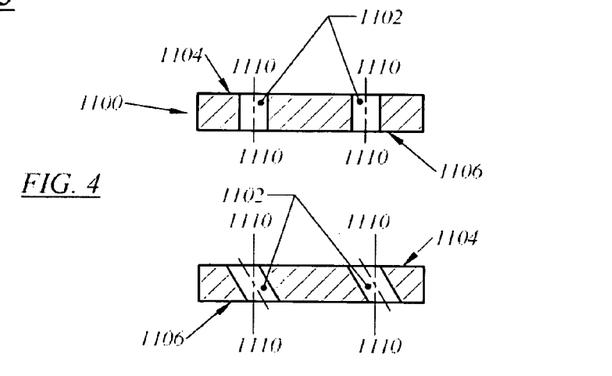
FIG. 4 is a cross section of an embodiment of a plate of the present invention.

With reference to FIG. 4, plate (1100) can include one or more bores (1102) where each bore (1102) is perpendicular to outward side (1104) and inward side (1106) of plate (1100) or plate (1100) can include one or more bores (1102) that are angled at other than perpendicular from the outward side (1104) and inward side (1106) of plate (1100). By way of example, bores (1102) can be angled from about 1 degree to about 60 degrees away from the bore's reference axis (1110), where the reference axis (1110-1110) equates to the perpendicular axis between outward side (1104) and inward side (1106) of plate (1000). Plate (1200) and one or more bores (1202) are manufactured in a similar fashion to plate (1100) and one or more bores (1102).

In select preferred embodiments, bores (1102) of plate (1100) are angled upward from outward side (1104) through inward side (1106) of plate (1100) and bores (1202) of plate (1200) are angled downward from the outward side of plate (1200) through the inward side of plate (1200) One or more bores (1102, 1202) function to receive a fastener, such as a screw (not shown in this view) that assists in securing the implant to bone.

Figure 5:
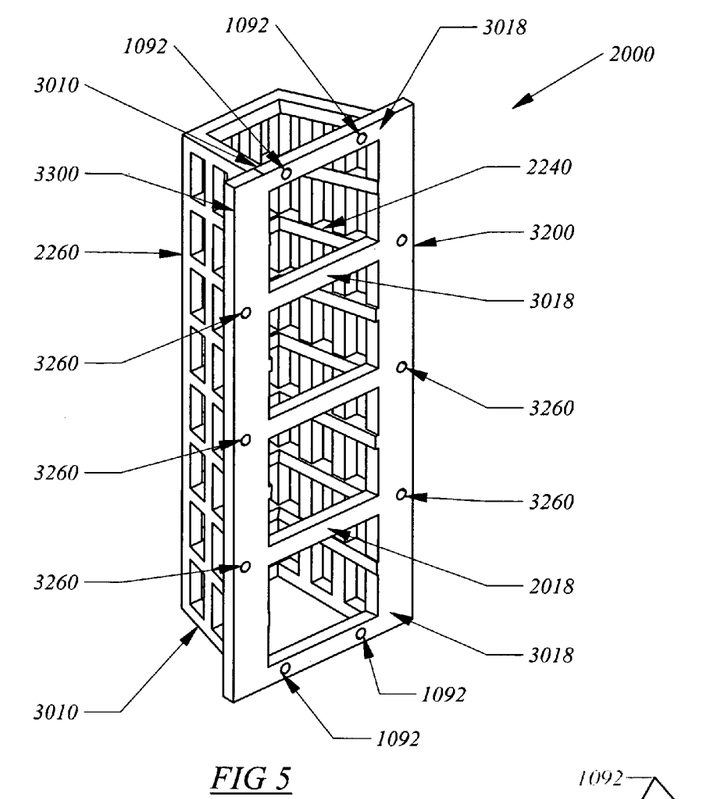
FIG. 5 is a frontal perspective of yet another embodiment of the present invention.

The preferred embodiment disclosed in FIG. 5 is similar to the preferred embodiment disclosed in FIGS. 1 and 3. The FIG. 5 embodiment portrays cage (2000) including first lateral brake (3200) and second lateral brake (3300). First lateral brake (3200) extends laterally beyond first lateral support (2240) of cage (2000) and second lateral brake (3300) extends laterally beyond lateral support (2260) of cage (2000). First lateral brake (3200) and second lateral brake (3300) are provided with one or more bores (3260).

Figure 6:
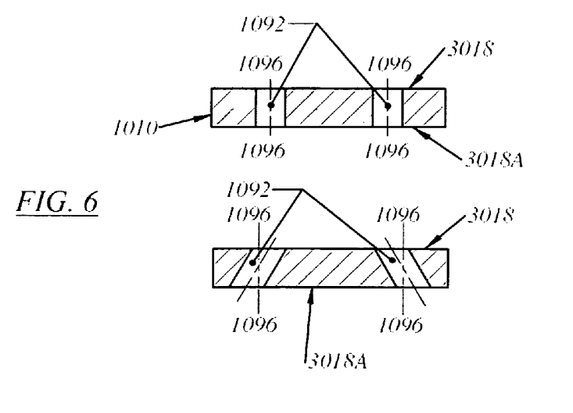
FIG. 6 is a cross section of an embodiment of an outward side and inward edge of a superior or inferior brace of the present invention.

With reference to the preferred embodiments portrayed in FIGS. 5 and 6, implant (2000) is provided with superior member (3010) of the series of trapezoidal braces (2010 and 3010) that includes a plurality of bores (1092) integral with outward side (3018) and inward edge (3018A) of superior member (3010). Inferior member (3010) of the series of trapezoidal braces (2010 and 3010) includes a plurality of bores (1092) integral with outward side (3018) and inward edge (3018A) of inferior member (3010). Bores (1092) are inset from first lateral support (2240) and second lateral support (2260) of cage (2000).

As depicted in FIG. 6, superior member (3010) includes one or more bores (1092) where each bore (1092) is angled at other than perpendicular from the outward side (3018) and inward edge (3018A) of superior member (3010). Bores (1092) can be angled from about 1 degree to about 60 degrees away from the bore's reference axis (1096-1096), where the reference axis (1096-1096) equates to the perpendicular axis between outward side (3018) and inward edge (3018A) of brace (3010). Inferior member (3010) and bores (1092) are manufactured in a similar fashion to superior member (3010) and one or more bores (1092). In the preferred embodiments, bores (1092) of superior member (3010) are angled upward from outward side (3018) through inward edge (3018A) of superior member (3010) and bores (1092) of inferior member (3010) are angled downward from the outward side (3018) through inward edge (3018A) of inferior member (3010). Bores (1092) function to receive a fastener, such as a screw (not shown in this view) that assists in securing the implant to bone.

Figure 7:
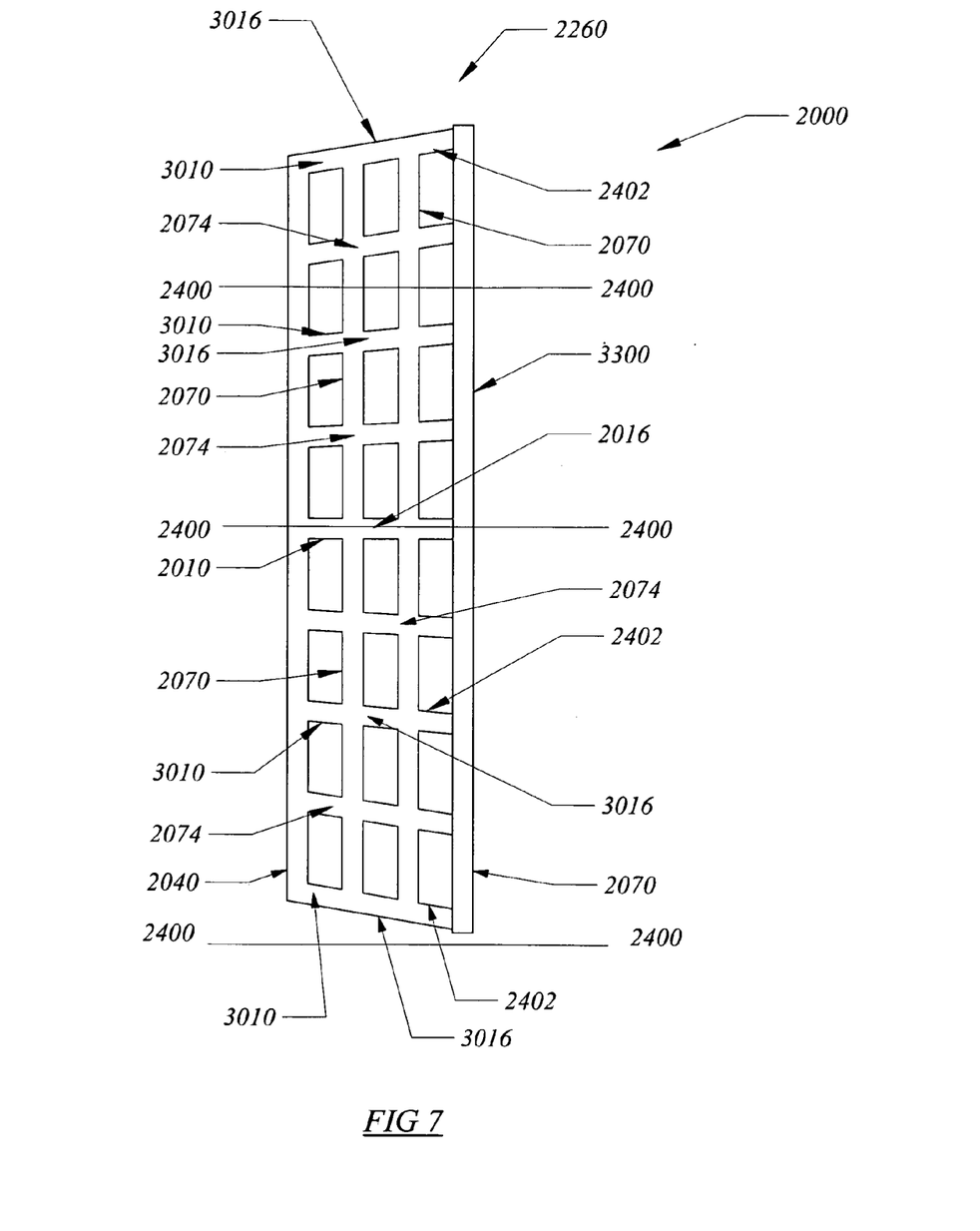
FIG. 7 is a side view of an embodiment of a lateral support of the present invention.

FIG. 7 is a lateral view of an embodiment of second lateral support (2260) of a preferred embodiment of implant (2000). Although not shown in this view, for this preferred embodiment, first lateral support (2240) is identical to second lateral support (2260). As shown, second lateral support (2260) includes universal corner post (2040), universal posts (2070), second lateral side (2016) of straight brace (2010), second lateral sides (3016) of first set of angled braces (3010), second lateral sides (3016) of second set of angled braces (3010) and ties (2074). Second lateral brake (3300) is also portrayed.

With respect to FIG. 7, axis lines 2400-2400 represent horizontal. Inward sides of angled braces (3010) are closer to straight brace (2010) than outward sides of angled braces (3010). Each angled brace (3010) of the first set of angled braces (3010) diverges toward the straight brace or generally horizontal divider (2010) at angles (2402) from about 1 degree to about 10 degrees from horizontal. Each angled brace (3010) of the second set of angled braces (3010) diverges toward the straight brace or generally horizontal divider (2010) at angles (2402) from about 1 degree to about 10 degrees from horizontal.

Within the scope of the present invention, preferred embodiments enabled in FIGS. 1, 3 and 5 can be manufactured such that: 1) the first set of braces (3010) and the second set of braces are generally horizontal; 2) the first set of braces (3010) or the second set of braces (3010) can diverge toward the centralized brace (2010) while the non-diverging set of braces (3010) remains generally horizontal; or 3) the first set of braces (3010) and the second set of braces (3010) diverge toward the centralized brace (2010).

In accordance with the present invention, among other things, it has been discovered that the current implant's wedge-like cage structure is beneficial because the wedge-like structure increases contact surface area between the implant and tissue surrounding the surgically created cavity. The increased contact area enhances spinal stabilization while the increased rigidity improves bony fusion. Testing has also revealed that the cage's wedge-like structure is capable of withstanding greater compressive loads than round or oval implants.

Figure 8:
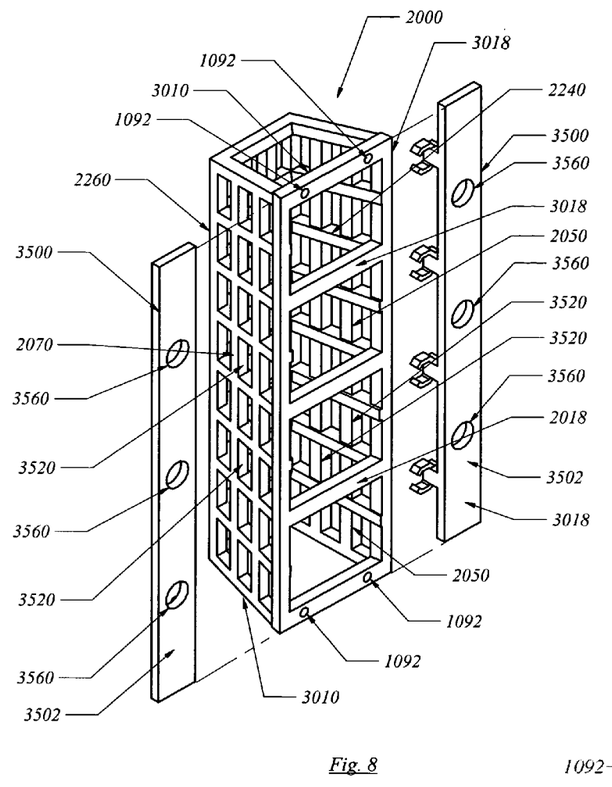
FIG. 8 is an exploded view of a cage utilizing a pair of connectable lateral brakes.

In many respects, the preferred embodiment disclosed in FIG. 8 is similar to the preferred embodiment disclosed in FIGS. 1, 3 and 5. FIG. 8 is an exploded view of cage (2000) that utilizes a pair of connectable lateral brakes (3500). When connected to cage (2000), connectable lateral brakes (3500) extend laterally beyond lateral supports (2240 and 2260), respectively, of cage (2000). Preferred embodiments of connectable lateral brakes (3500) are provided with one or more bores (3560). Among other things, FIG. 8 portrays outward sides (3502) of connectable lateral brakes (3500).

Figure 9:
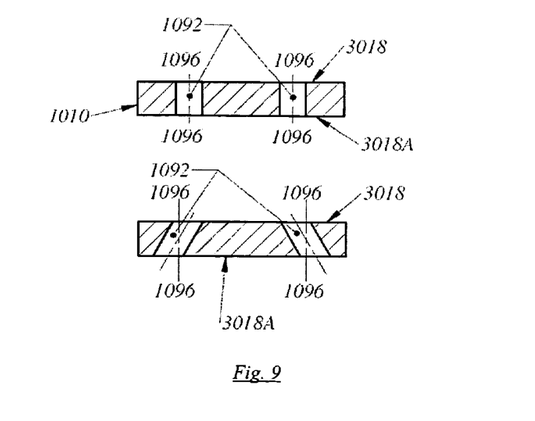
FIG. 9 is a cross section of an embodiment of a brake of the present invention.

With reference to the preferred embodiments portrayed in FIGS. 8 and 9, implant (2000) is provided with superior member (3010) of the series of trapezoidal braces (2010 and 3010) that includes a plurality of bores (1092) integral with outward side (3018) and inward edge (3018A) of superior member (3010). Inferior member (3010) of the series of trapezoidal braces (2010 and 3010) includes a plurality of bores (1092) integral with outward side (3018) and inward edge (3018A) of inferior member (3010). Bores (1092) are inset from first lateral support (2240) and second lateral support (2260) of cage (2000).

As depicted in FIG. 9, superior or inferior member (3010) can include one or more bores (1092) that is perpendicular from the outward side (3018) and inward edge (3018A) of superior member (3010). Bores (1092) can also be angled from about 1 degree to about 60 degrees away from the bore's reference axis (1096-1096), where the reference axis (1096-1096) equates to the perpendicular axis between outward side (3018) and inward edge (3018A) of brace (3010). In the preferred embodiments, bores (1092) of superior member (3010) are angled upward from outward side (3018) through inward edge (3018A) of superior member (3010) and bores (1092) of inferior member (3010) are angled downward from the outward side (3018) through inward edge (3018A) of inferior member (3010). Bores (1092) function to receive a fastener, such as a screw (not shown in this view) that assists in securing the implant to bone.

Figure 10:
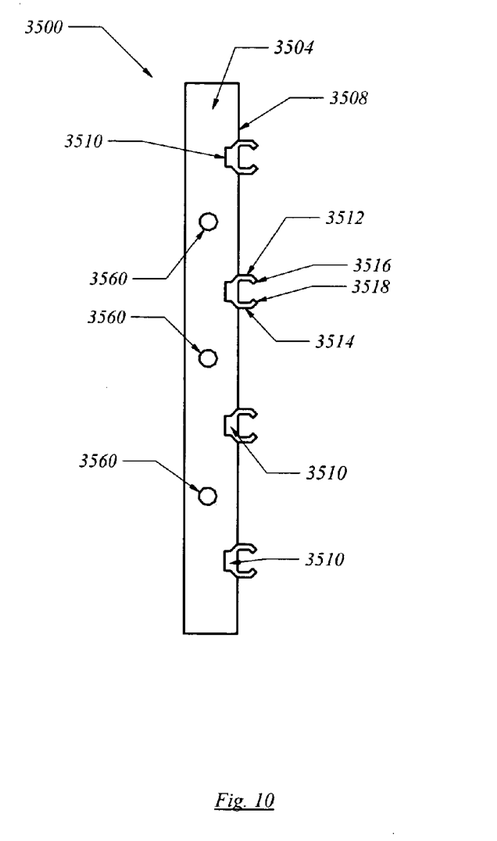
FIG. 10 is a perspective of the inward side of a connectable lateral brake.

FIG. 10 is a perspective of inward side (3504) of a connectable lateral brake (3500). Attached to inward side (3504) of connectable lateral brake (3500) are connectors (3510) for connecting connectable lateral brakes (3500) to first lateral support (2240) and/or second lateral support (2260) of cage (2000). Although other means can be used to secure connectable lateral brakes (3500) to implant (2000), in FIG. 10, clips (3510) are enabled. Clip (3510) includes first projection (3512) and second projection (3514) that extend beyond edge (3508) of connectable lateral brake (3500). Tips (3516 and 3518) of clips (3510) are biased toward each other such that when clips (3510) are forced about either a universal post (2050) of first lateral support (2040) and/or a universal post (2070) of second lateral support (2260), connectable lateral brakes (3500) are secured to cage (2000). In select preferred embodiments projections, (3512 and 3514) of clips (3510) are engineered to have dimensions that virtually fill spaces (3520) proximate to universal posts (2050) and/or (2070) where clips (3510) have been attached. By way of illustration and not limitation, clips or connectors (3510) can have a height of about 2 millimeters, a depth of 4 millimeters and a width of about 2 millimeters.

Figure 11:
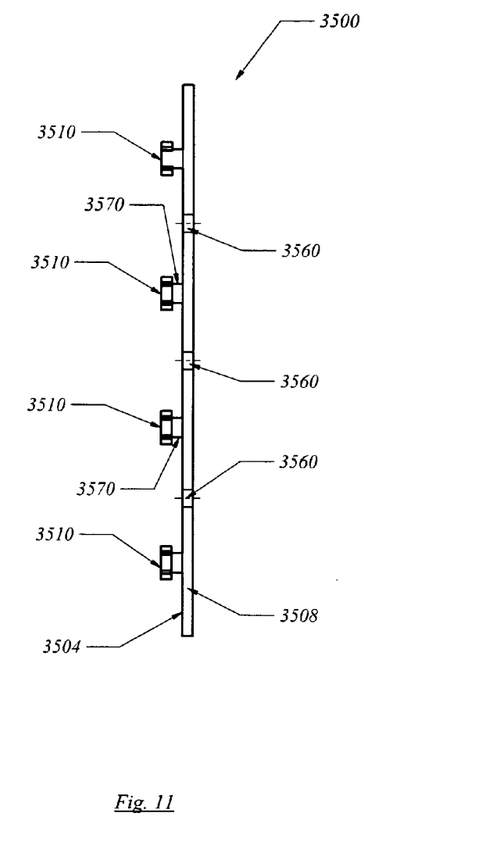
FIG. 11 is a frontal view of an edge of the connectable lateral brake.

FIG. 11 is a frontal view of edge (3508) of connectable lateral brake (3500). Arm (3570) is attached to inward side (3504) of connectable lateral brake (3500) and connector (3510). Welds or any other means acceptable in the art can attach arm (3570) to inward side (3504) and connector (3510). In select preferred embodiments, arm (3570) extends clip (3510) for a length from inward side (3504) such that clip (3510) is positioned for secure engagement with universal posts (2050) and/or (2070), other than the outermost universal posts (2050) or (2070), and spaces (3520) of first lateral support (2240) and/or second lateral support (2260) of cage (2000).

Figures 12, 13:
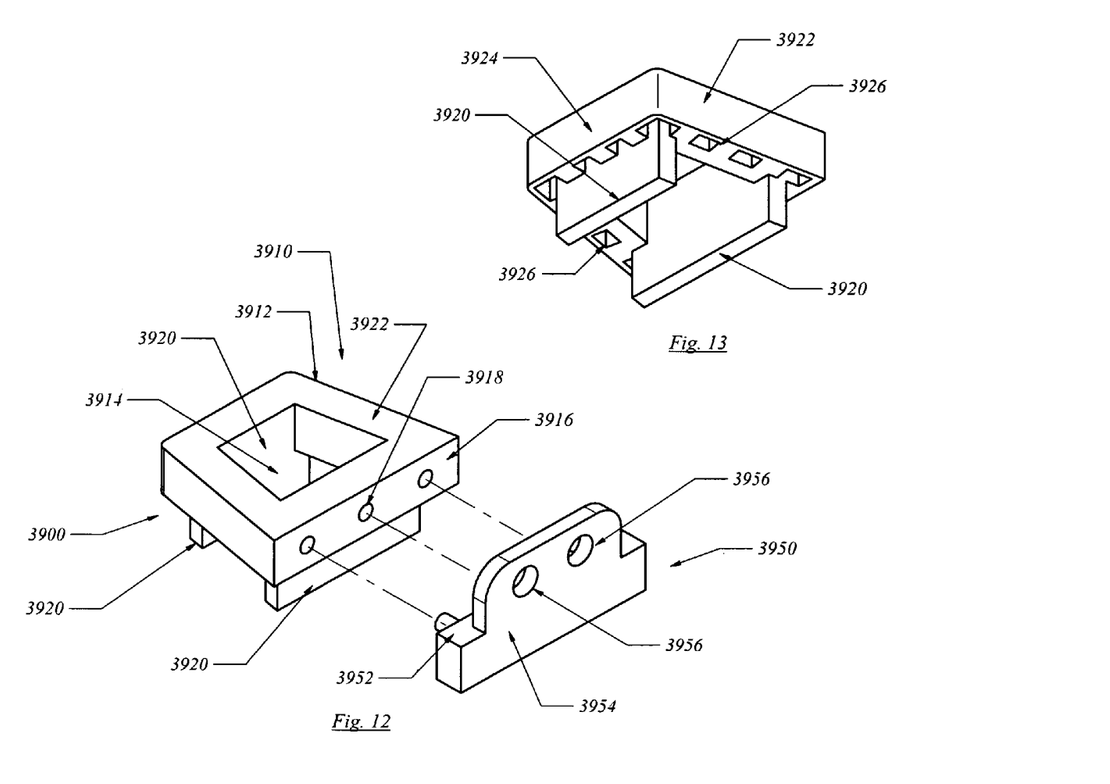
FIG. 12 is an exploded frontal perspective that enables and shows an end cap.
FIG. 13 is a plan view of implant proximate surface opposite implant distal surface of the outermost section of a bridge.

FIG. 12 is an exploded frontal perspective that enables and shows an end cap (3900). End cap (3900) can assist in securing the spinal implant to vertebra. As shown in FIG. 12, end cap (3900) comprises bridge (3910) and coupler (3950).

Bridge (3910) has outermost section (3912) that surrounds a generally trapezoidal aperture (3914). Surgeon facing side (3916) of outermost section (3912) is provided with a plurality of bores (3918). As shown in FIG. 12, surgeon facing side (3916) of bridge (3910) is provided with three bores (3918), but other embodiments of surgeon facing side (3916) can be provided with one or more bores (3918).

Preferred embodiments of bridge (3910) are provided with two or more docking slides (3920) that extend from outermost section (3912) of bridge (3910) toward a corresponding opening proximate a lengthwise end of the spinal implant (not shown in this view). Docking slides (3920) are engineered to securely fit within the corresponding opening proximate a lengthwise end of the spinal implant.

FIG. 13 is a perspective of end cap (3900) and implant proximate surface (3924) opposite implant distal surface (3922) of outermost section (3912) of bridge (3910). Select embodiments of implant proximate surface (3924) of bridge (3910) are provided with bores (3926). Bores (3926) can reciprocate with spikes of the spinal implant (not shown in this view).

Returning to FIG. 12, coupler (3950) includes spacer (3952) and frontal plate (3954). Frontal plate (3954) is provided with holes (3956) capable of receiving fasteners (not shown in this view).

Figure 14:
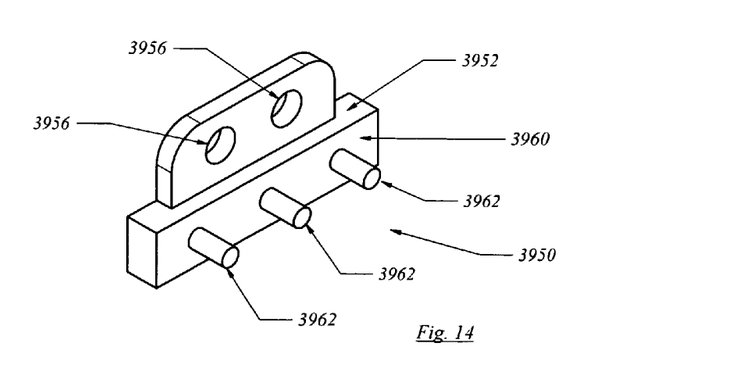
FIG. 14 is a perspective view of bridge facing side of a coupler.

FIG. 14 is a perspective view of bridge facing side of coupler (3950). Inward side (3960) of coupler (3950) is provided with three pins (3962) corresponding to bores (3918) of surgeon facing side (3916) of outermost section (3912) of bridge (3910). Pins (3962) are attached to inward side (3960) in any manner acceptable in the art. As shown in FIG. 14, coupler (3950) is provided with three pins (3962), but other embodiments of coupler (3950) can be provided with one or more pins (3962).

Figure 15:
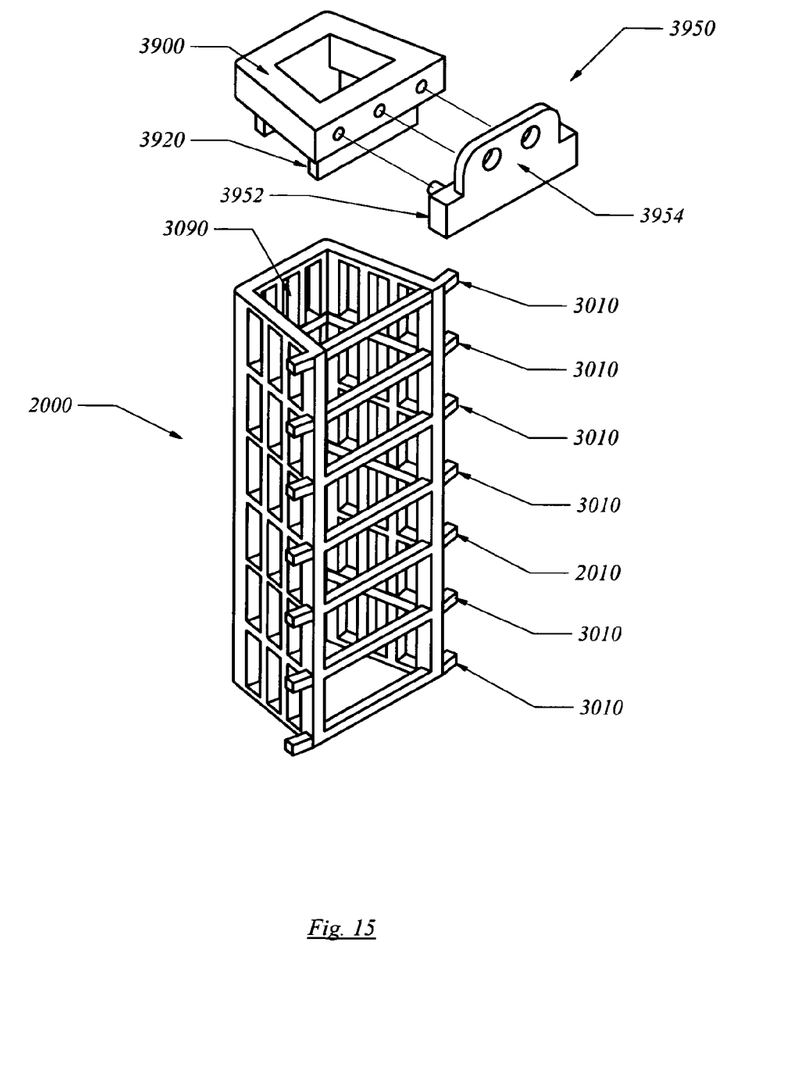
FIG. 15 is an exploded view of a preferred embodiment of an end cap and a cage.

FIG. 15 is an exploded view of a preferred embodiment of an end cap (3900) and cage (2000). As shown, end cap (3900) is attached to superior brace (3010) of cage (2000). Docking slides (3920) securely fit within trapezoidal opening (3090) of cage (2000). Spacer (3952) of coupler (3950) causes frontal plate (3954) to be anterior to cage (2000). Fasteners (not shown in this view), such as screws, are inserted through holes (3956) to secure end cap (3900) to vertebra (not shown in this view). End cap (3900) is compatible with either inferior or superior trapezoidal openings (3090) of cage (2000).

Preferred embodiments of outermost section (3912) of bridge (3910) of end cap (3900) can have a height or thickness of from about 2 millimeters to about 5 millimeters. In select preferred embodiments, the thickness of outermost section (3912) is a consistent height. In other preferred embodiments, outermost section (3912) of bridge (3910) is provided with surgeon facing side (3932) of greater thickness than vertebra proximate side (3934). In some preferred embodiments, lateral sides of outermost section (3912) of bridge (3910) can taper between surgeon facing side (3932) and vertebra proximate side (3934).

Figure 16:
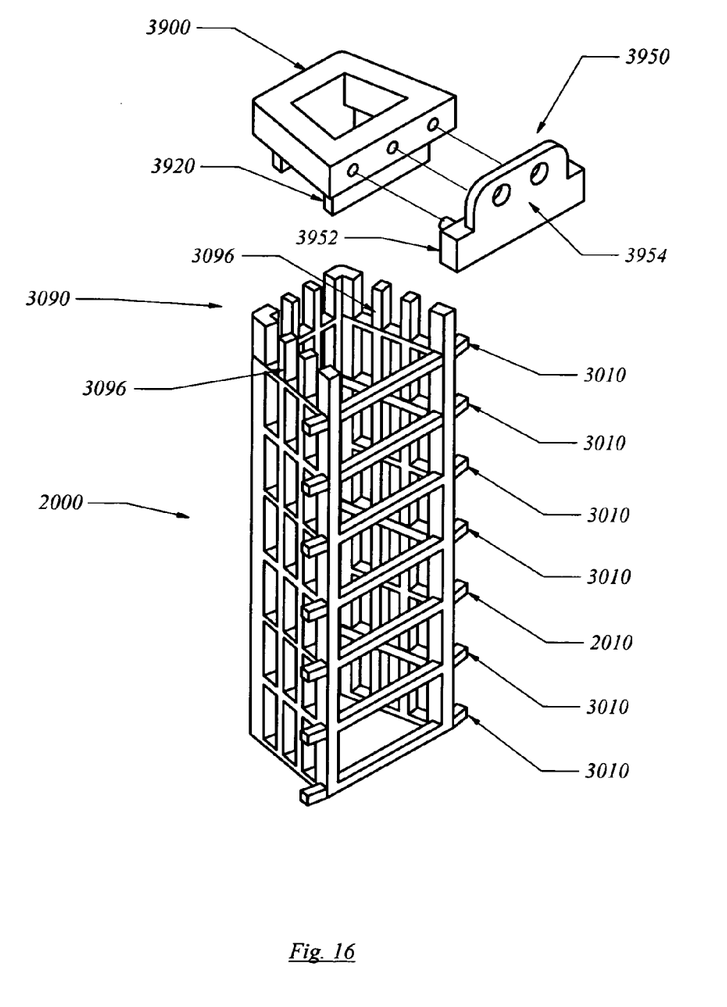
FIG. 16 is an exploded view of another preferred embodiment of an end cap and a cage.

FIG. 16 is an exploded view of another preferred embodiment of an end cap (3900) and cage (2000). Spikes (3096) are created when cage (2000) is severed along a longitudinal section generally parallel brace (3010). Although not shown in this view, bores (3926) of bridge (3910) reciprocate with spikes (3096) as docking slides (3920) slide into trapezoidal opening (3090) to secure end cap (3900) to cage (2000). Spacer (3952) of coupler (3950) causes frontal plate (3954) to be anterior to cage (2000). Fasteners (not shown in this view) are inserted through holes (3956) to secure end cap (3900) to vertebra (not shown in this view). Embodiments of end cap (3900) are compatible with either inferior or superior trapezoidal openings (3090) of cage (2000).

The coupling of end cap (3900) and cage (2000) effectively increases the length of the spinal implant. In select preferred embodiments, the combination of end cap (3900) and cage (2000) can assist in creation of lordosis at one or more ends of the spinal implant. When connected to vertebra, end cap (3900) can also enhance stability of the spinal implant.

Figure 17:
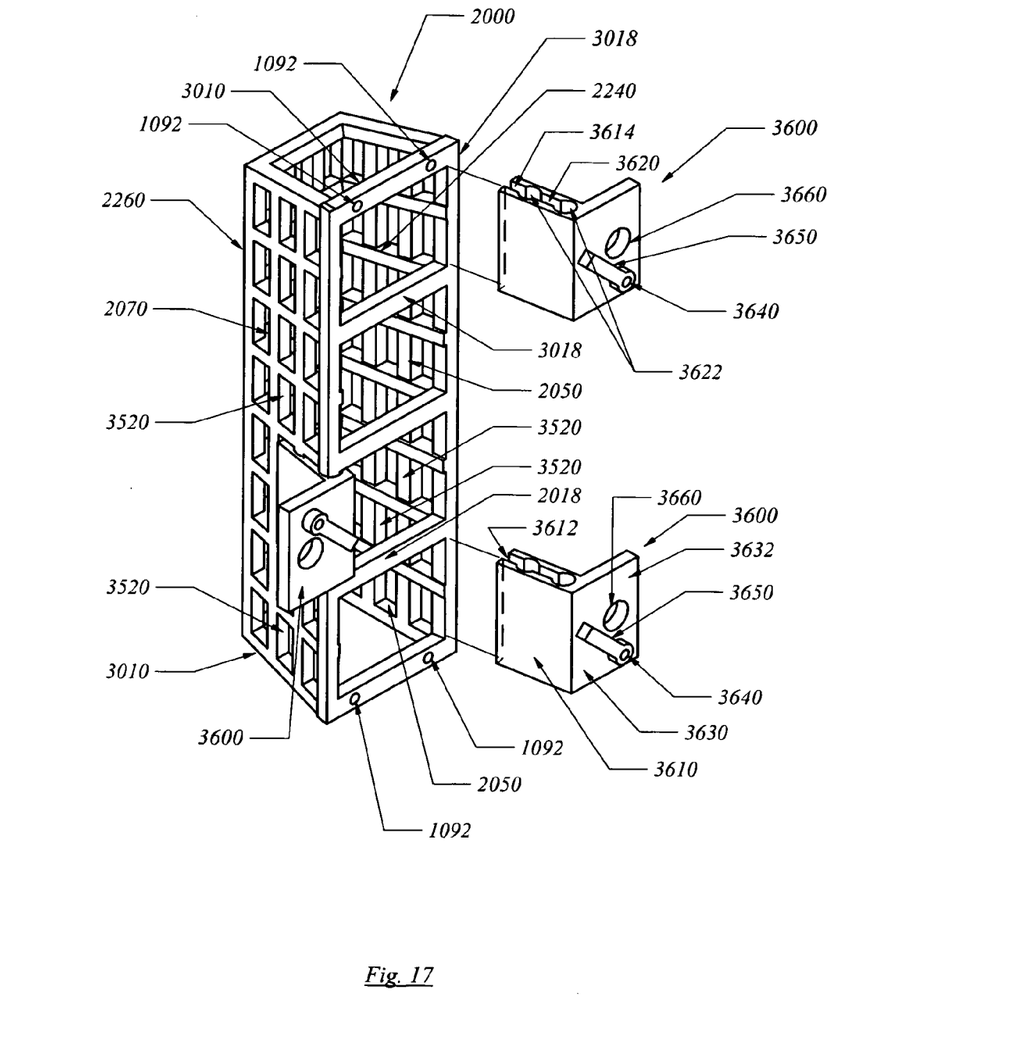
FIG. 17 is an exploded view of cage and a plurality of attachable lateral brakes.

FIG. 17 is an exploded view of cage (2000) and a plurality of attachable lateral brakes (3600). When connected to cage (2000), connectable lateral brakes (3600) extend laterally beyond lateral supports (2240 and 2260), respectively, of cage (2000). Connectable lateral brake (3600) has first wall (3610) and second wall (3630) that is generally perpendicular to first wall (3610). First wall (3610) has an open side (3612) in communication with channel (3614) that extends through the length of first wall (3610). Channel (3614) has a first width (3620) that is narrower than universal posts (2050, 2070) and a second width (3622) that is greater than universal posts (2050, 2070) of first lateral support (2240) or second lateral support (2260) of cage (2000). Second width (3622) locks about the perimeters of universal posts (2050, 2070) to secure first wall (3610) to cage (2000). Second wall (3630) is provided with hub (3640) attached to outward side (3632) of second wall (3630). Rotatable safety (3650) is attached to hub (3640) and is capable of covering at least a part of the circumference of bore (3660) for preventing a fastener (not shown in this view) from backing out of bore (3660). Other reference numbers shown in FIG. 17 are identical to the reference numbers shown in FIG. 8.

Having disclosed the invention as required by Title 35 of the United States Code, Applicant now prays respectfully that Letters Patent be granted for his invention in accordance with the scope of the claims appended hereto.

What is claimed is:

1. A spinal implant and an end cap for said spinal implant combination; said combination comprising:
   a) said spinal implant;
   b) a coupler comprising:
      i) a spacer;
      ii) a frontal plate including at least one opening for receiving a fastener for securing said coupler to vertebrae; and
      iii) pins attached perpendicularly to and extending away from an inward side of said spacer; and
   c) a bridge comprising:
      i) an outermost section surrounding a generally trapezoidal aperture; said outermost section further comprising;
         A) a surgeon facing side including a plurality of bores receiving said pins; and
         B) a spinal implant facing side including bores therein; and
      ii) docking slides for securely engaging a corresponding opening proximate a lengthwise end of said spinal implant.

2. A spinal implant and an end cap for said spinal implant combination; said combination comprising:
   a) said spinal implant further comprising:
      i) a cephalic lengthwise end and a caudal lengthwise end;
      ii) a length greater than said spinal implant's width or said spinal implant's depth; and
      iii) an opening associated with one of said lengthwise ends of said spinal implant;
   b) a coupler comprising:
      i) a frontal plate including at least one opening for receiving a fastener for securing said coupler to vertebrae; and
      ii) one or more extensions; and
   c) a bridge comprising:
      i) bores receiving said extensions; and
      ii) slides securely engaging a portion of an inward perimeter of said opening associated with one of said lengthwise ends of said spinal implant.

3. The end cap of claim 2, wherein said coupler further comprises a spacer.

4. The end cap of claim 3, wherein said bridge further comprises a spinal implant facing side including bores therein.

* * * * *